United States Patent [19]

Brand et al.

[11] Patent Number: 5,131,260
[45] Date of Patent: Jul. 21, 1992

[54] DEVICE AND METHOD FOR THE CONTINUOUS MEASUREMENT OF THE AMMONIA CONCENTRATION IN GASES IN THE PPM RANGE

[75] Inventors: Reinhold Brand; Bernd Engler, both of Hanau; Wolfgang Honen, Kusterdingen-Jettenburg; Edgar Koberstein, Alzenau, all of Fed. Rep. of Germany

[73] Assignee: Degussa AG, Frankfurt am Main, Fed. Rep. of Germany

[21] Appl. No.: 676,707

[22] Filed: Mar. 29, 1991

[30] Foreign Application Priority Data

Mar. 31, 1990 [DE] Fed. Rep. of Germany ....... 4010425

[51] Int. Cl.$^5$ .......................................... G01N 30/00
[52] U.S. Cl. ..................... 73/23.2; 73/31.07; 73/31.05; 55/70; 55/90; 55/91; 55/84
[58] Field of Search ............... 73/23.35, 23.39, 23.4, 73/23.41, 23.42, 31.05, 25.03, 23.2, 31.07; 55/67, 80, 386, 191, 70, 81, 84, 85, 257.1, 389, 90, 91, 95, 244

[56] References Cited

U.S. PATENT DOCUMENTS

| | | | |
|---|---|---|---|
| 2,091,630 | 8/1937 | Fenske et al. | 55/70 |
| 2,431,455 | 11/1947 | Blanding | 55/90 |
| 2,808,125 | 10/1957 | Buck et al. | 55/70 |
| 3,122,594 | 2/1964 | Kielback | 55/90 |
| 3,334,514 | 8/1967 | Catravas | 73/23.35 |
| 4,183,902 | 1/1980 | Hashimoto et al. | 55/90 |
| 4,778,490 | 10/1988 | Pollert | 55/70 |
| 5,005,399 | 4/1991 | Holtzclaw et al. | 73/23.39 |
| 5,064,450 | 11/1991 | Lankton et al. | 55/70 |

FOREIGN PATENT DOCUMENTS 3729891 3/1989 Fed. Rep. of Germany ..... 73/23.39

Primary Examiner—Hezron E. Williams
Assistant Examiner—Michael Brock
Attorney, Agent, or Firm—Beveridge, DeGrandi & Weilacher

[57] ABSTRACT

A device for the continuous measurement of the ammonia concentration in gases in the ppm range includes a columnar absorption vessel (1) with a hemispherical bottom (4). The bottom of the column includes an overflow (3) and an outlet (5). The gas introduction pipe (7,8) empties above the bottom (4) and below a sieve bottom (6) arranged in the column (1). A packing material (10) rests on the sieve bottom (6), which packing (10) essentially fills the absorption column (1). A cooling part (11) extends from the absorption column (1). The cooling part (11) includes a cooling zone (15) and a gas collection space (16) above it with a closable connection piece (13). A pipe (14), which may include a serrated crown on each end, runs from the gas collecting space (16) downward in a cooled manner to the packing 10. The liquid absorption agent is introduced through a lateral connection piece (18) into the gas collection space (16). For the measurement of ammonia concentration, a certain volume flow of the gas to be measured is washed in a countercurrent flow with the absorption agent, and the NH$_3$ content is determined in a part of the ammonia containing absorption agent. The volume flow rate of the absorption agent and of the gas from which NH$_3$ has been removed is measured (the latter being dried), and the ammonia concentration is thereby calculated.

21 Claims, 2 Drawing Sheets

DEVICE AND METHOD FOR THE CONTINUOUS MEASUREMENT OF THE AMMONIA CONCENTRATION IN GASES IN THE PPM RANGE

BACKGROUND OF THE INVENTION

This invention relates to a novel device for the continuous measurement of the ammonia concentration ($NH_3$) in gases, for example, flue gases, in the ppm range. A method for the measurement of ammonia concentration is also described, which method can be carried out with the device of this invention.

The quantitative determination of the ammonia concentration in a gaseous media has become important due to the introduction of secondary measures for the removal of nitrogen (i.e. denitrofication) from furnace systems. In most instances, the process of selective catalytic reduction (SCR) with ammonia as the reducing agent is used for lowering the nitrogen oxide content of the flue gases. The continuous measurement of ammonia content is desirable for controlling such systems and for monitoring the prescribed emission values of the gases.

Devices for measuring the concentration of ammonia are currently known which are based on various methods and principles and are suitable for various measurement ranges.

A distinction can be made between methods which detect the $NH_3$ directly in the gaseous phase and those in which $NH_3$ is chemically bound and then determined in solution. Methods in which the $NH_3$ concentration can be determined directly in the gaseous phase are usually based on the photometry of the $NH_3$ in the infrared (IR) range. In these methods, the intensity of light (preferably infrared light) absorbed in, transmitted by, or reflected from a gaseous sample may be quantitatively measured and compared against a reference light intensity, to thereby provide a quantitative measurement of ammonia concentration in the gaseous sample. In these methods, specimen gas is removed from a flue-gas line via a gas probe and conducted into a cuvette of a photometer. The lowest measuring range of most of the commercially available devices is in the range of about 0–300 ppm.

The range between 0 and 10 ppm ammonia, which is, for example, downstream of the catalyst and particularly interesting in the monitoring of denox systems (i.e. systems for freeing flue gases from $NO_x$, according to Ernst), cannot be reliably determined by the devices and methods described above. However, laser photometers have become commercially available wherein $NH_3$ concentrations around 1 ppm can be determined in situ. However, these laser devices are extremely expensive, require a long absorption stretch and exhibit high variations of errors.

Another method for determining the $NH_3$ concentration in a gaseous phase is based on the combustion of the $NH_3$ on a catalyst and then measuring the heat of the reaction. This method is reliable only at higher concentrations of $NH_3$ and in the absence of further oxidizable substances, for example, carbon monixide and hydrocarbons.

Methods in which $NH_3$ is chemically bound from the gaseous phase and the concentration of $NH_3$ then determined in solution are used more frequently, since these methods are more sensitive. However, these methods have the disadvantage of being more time-consuming and are usually operated in a discontinuous manner.

In addition, calorimetric methods are often used in which a quantitative measurement of the light absorption of a dye material which arises in a color reaction with $NH_3$ and other reagents is used to determine concentration of ammonia.

Other frequently used methods for determining ammonia concentration are ion-sensitive potentiometry and the conventional wet-chemical determination of $NH_3$ per acid-base titration after a Kjeldahl distillation. However, these methods are also discontinuous and usually require a considerable amount of time until the complete result of the analysis is available. Other, less frequently used methods make use of the photoionization of $NH_3$ and/or the use of electrochemical sensors. however, the desired measuring range between about 0 and .10 ppm ammonia cannot be achieved by these methods.

SUMMARY OF THE INVENTION

The invention relates to a device and method for measuring the ammonia concentration in a gaseous sample. By using this invention, very low concentrations of ammonia may be measured.

It is a further objective of this invention to provide a method and apparatus for measuring ammonia concentration in a continuous manner.

The apparatus of the invention includes a columnar absorption vessel wherein the ammonia containing gaseous sample is admitted near the bottom of the absorption vessel. This ammonia containing gas meets a counter-current flow of an absorbent liquid in a packed region of the absorption vessel. The absorbent liquid enters the column near its top end. The ammonia component of the gaseous sample is absorbed by the liquid and collected at the bottom of the vessel. From the bottom of the vessel, the liquid is pumped to an ammonia analyzer, and the content of ammonia in the absorbent liquid component is determined in the ammonia analyzer.

The ammonia free gas is removed from the top of the absorption vessel, dried, and passed through a gas meter. The as meter measures the volume flow rate of the gas passing through the column.

The ammonia concentration in the gas sample may be determined based on the measured concentration of ammonia in the absorbent liquid and the volumetric flow rate of the ammonia free carrier gas.

BRIEF DESCRIPTION OF THE DRAWINGS

The invention will be more fully described in the following detailed description, especially when considered in view of the attached figures, wherein.

In the FIGS., like reference numbers refer to same part throughout the various views shown.

DETAILED DESCRIPTION OF THE INVENTION

Figure 1:
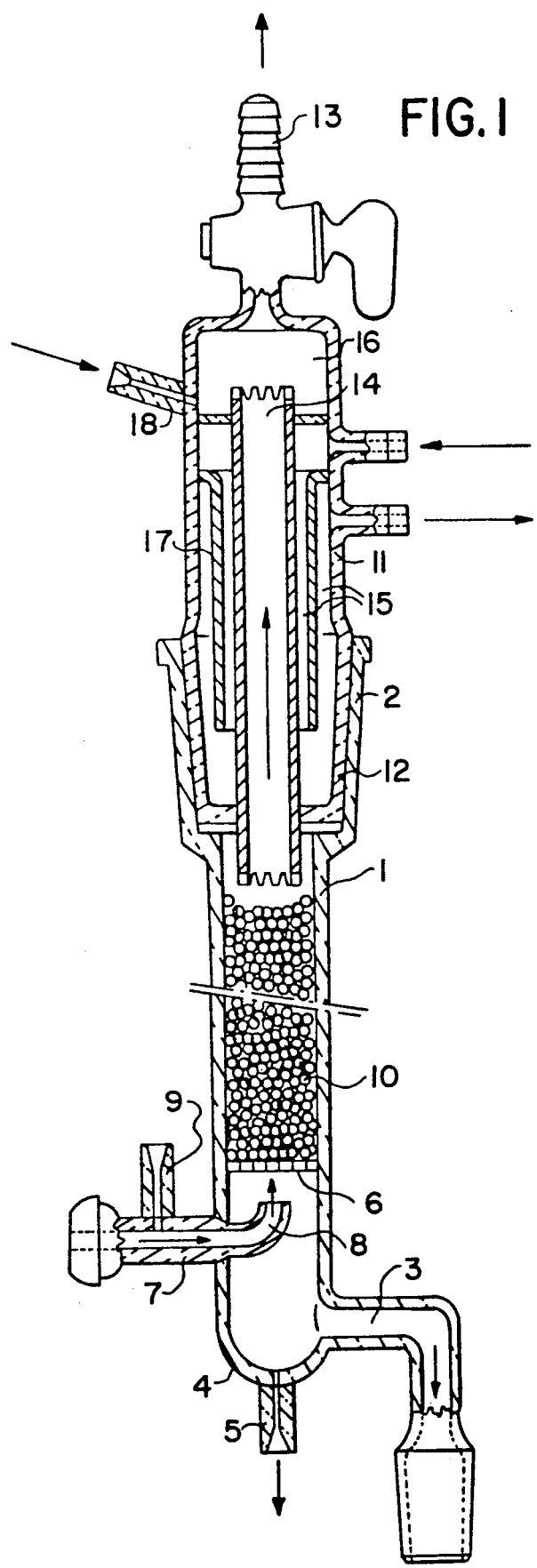
FIG. 1 shows a sectional view of the columnar absorption vessel in accordance with the invention.

The columnar absorption vessel 1 and cooling fixture 11 in accordance with the invention are shown in FIG. 1.

The subject invention as shown in FIG. 1 is constituted by a device for the continuous measurement of the ammonia concentration in gases in the parts per million (ppm) range. The device is characterized by a columnar absorption vessel 1 with a bottom 4 which bulges out as a hemisphere with an outlet piece 5 located at the lowest position in the column. An overflow pipe 3 is located laterally immediately above the bottom 4. An infeed pipe 7, 8 for the introduction of the gas whose concentration is to be measured is located laterally above the bottom 4 and below a sieve bottom 6 fastened in the vessel 1. The infeed pipe 7, 8 is bent upward in the central portion of the vessel 1 (with respect to the cross-section of the vessel) and is provided with a rinse line 9. Packing material 10 rests on the sieve bottom 6 and essentially fills up vessel 1. A cooling fixture 11 (or cooling part) extends from the absorption vessel 1 in an upward direction. The cooling part 11 includes a cooling zone 15, and a gas collection chamber 16. Located over the gas collection chamber 16 is a closable suction piece 13. A connection piece 18 for supplying the liquid absorption agent laterally into space 16 is provided. An inner pipe 14, which may be designed with a serrated crown on one or both of its ends, runs through cooling zone 15, and extends with its mouth into the gas collection chamber 16. The inner pipe 14 is tightly connected at its other end beneath the cooling zone 15 to the jacket of cooling part 11.

A preferred embodiment of the device in accordance with the invention provides that absorption vessel 1 and the cooling part 11 are designed as separate and individual pieces which can optionally be connected to one another via ground-glass joints.

In addition, the invention includes a method for the continuous meausrement of the ammonia concentration of gases in the ppm range which can be carried out using the device described above. The method is characterized in that a certain volumetric flow rate of the gas whose ammonia concentration is to be measured is continuously brought into contact with a countercurrent flow of a liquid absorption agent. At least a part of the ammonia-charged absorption agent is quantitatively tested in an ammonia analyzer for its $NH_3$ concentration. The total volume flow of the absorption agent and the volume flow of the gas freed of ammonia and dried is measured, and the $NH_3$ concentration calculated according to the formula:

$$c^G_{NH3} = \frac{C^L_{NH3} \times V_{Abs} \times 10^6 \times V_{M,NH3}}{V_G \times M_{NH3}} \text{ (ppm)}$$

which:
- $C_{NH3}^G$ represents the concentration of $NH_3$ in the gas (in ppm relative to dry);
- $C_{NH3}^L$ represents the concentration of $NH_3$ in the absorption solution (g/dm$^3$)
- $V_{Abs}$ represents the volume flow of the flowing absorption solution (dm$^3$/h);
- $V_G$ represents the volume flow of the gas to be analyzed, drawn by suction through the absorption vessel (dm$^3$/h) in a normal state relative to dry; normal state refers to a pressure of 1 bar at 0° C or 273.15K);
- $V_{M, NH3}$ represents the molar volume of gaseous ammonia (dm$^3$/mole in a normal state); and
- $M_{NH3}$ represents the molar mass of ammonia (g/mole).

A preferred embodiment of the apparatus in accordance with the invention is shown in FIG. 1 and has the following design. All dimensions and materials set forth in this specification are for illustrative purposes only and should not be considered to limit the invention. Various modifications and changes can be made and are deemed to be within the level of ordinary skill in the art.

The apparatus includes a cylindrical columnar absorption vessel 1 made of glass with an inner diameter of about 14.4 mm and a length of about 225 mm. The absorption column 1 carries a standard socket 2 (female tapered joint; NS 29 according to DIN 12242, part 1) on its upper end. Vessel 1 is equipped with a lateral overflow pipe 3 which extends horizontally from the vessel 1 at first and then bends downward into an L-shape. The end of the overflow pipe 3 is provided with a socket (NS 14) for the insertion of a collector flask (not shown) for collecting the $NH_3$-containing absorption agent whose ammonia content is not measured. The overflow pipe 3 is located above the bottom 4 of the vessel 1, which bottom 4 is bulged out in a downward direction as a hemisphere. A discharge piece 5 for removing the $NH_3$-charged absorbent liquid by suction, is attached at the lowest point of the bottom 4. This absorbent liquid is later analytically measured for ammonia content.

A sieve bottom 6 with round perforations which are approximately 2 mm in diameter is located approximately 170 mm below the standard socket 2. Connection piece 7 for introducing the gas to be analyzed empties readially into the bottom area of the glass cylinder which makes up the absorption vessel 1, approximately 11 mm below the sieve bottom 6. Glass pipe 8, which is bent up into an L-shape and terminates after a short distance, forms the continuation of the connection piece 7 in the interior of the glass cylinder. As a result of the arrangement of the glass pipe 8, the gas to be analyzed is directed directly onto the bottom of the sieve bottom 6. This prevents the drying out of the glass walls of the absorption vessel by the test gas, which is typically at an elevated temperature.

A spherical ground-glass joint (for example, a ball-and-socket joint) is fastened to the outer end of connection piece 7 at a distance of approximately 24 mm from the jacket of the glass cylinder. Advantageously, this ground glass joint and the other ground glass joints used in this invention may be made from quartz glass. Sealants and/or lubricating materials may be placed between the ground glass surfaces in the joint. Such ground glass joints are well known to those skilled in the art and are commercially available.

An upwardly directed rinsing piece 9 is attached in the middle of connection piece 7. Some wash liquid can be introduced through this rinsing line 9 from time to time for rinsing (or washing) the gas entry piece 7. In the preferred embodiment of this invention, the wash fluid introduced through the rinse line 9 is the same as the absorbent liquid introduced in the top of the column.

A packing 10, which may be constructed in the form of balls, rings, hollow cylinders, or customary mixing and gas-exchange elements of ceramics, glass or plastic, essentially fills column 1 above the sieve bottom 6 to approximately the shoulder of socket 2.

A cooling part 11 is set on the socket 2 of the absorption vessel 1. The cooling part 11 is connected to the absorption column via cone 12 (male tapered joint NS 29) which is attached to the socket 2.

The cooling fixture 11 includes a partially double-walled cylindrical glass tube with a diameter of 26 mm and a length of approximately 90 mm. The glass tube terminates at the top in a one-way stopcock 13 which is connected by a line to a gas suction pump 22 (see FIG. 2). The gas freed of NH$_3$ in the absorption vessel 1 passes upward through the cooling fixture 11 from below and through an inner tube 14 with an inner diameter of 8 mm. The inner tube 14 terminates in a gas collection space 16 located above cooling zone 15. Inner tube 14 is preferably designed on both ends as a serrated crown.

Cooling zone 15 is designed like a Liebig condenser and equipped with a customary cooling-agent guide 17. Liebig condensers are well known to those skilled in the art and are commercially available. A connection piece 18 for supplying absorption liquid empties laterally into the gas collection space 16. The liquid runs over the upper serrated crown into the inner pipe 14 and then drips over the lower serrated crown onto the packing 10. The serrated crowns effect a loading of the packing 10 with the absorption liquid in as uniform a manner as possible. The inner pipe can be cooled, if necessary, through the double jacket with flowing water.

A stationary NH$_3$ concentration develops in the flowing wash liquid during the operation of the device after a short start up time of a few seconds. After the stationary NH$_3$ concentration has been established the NH$_3$ concentration in the gas to be analyzed can be calculated with the aid of the following formula:

$$C^G_{NH_3} = \frac{C^L_{NH_3} \times V_{Abs} \times 10^6 \times V_{M,NH_3}}{V_G \times M_{NH_3}} \text{ (ppm)}$$

in which:
$C_{NH_3}{}^G$ = concentration of NH$_3$ in the gas (ppm relative to dry);
$C_{NH_3}{}^L$ = concentration of NH$_3$ in the absorption solution (g/dm$^3$);
$V_{Abs}$ = volume flow of the flowing absorption solution (dm$^3$/h);
$V_g$ = volume flow of the gas to be analyzed, drawn by suction through the absorption vessel (dm$^3$/h in a normal state relative to dry);
$V_{M, NH_3}$ = molar volume of gaseous ammonia state (dm$^3$/mole in a normal state); and
$M_{NH_3}$ = molar mass of ammonia (g/mole).

In order to operate the NH$_3$ analyzer, its base line is first adjusted by drawing in fresh wash liquid by suction. Then, a calibration with an exactly adjusted standard solution of NH$_4$Cl in wash liquid (as a solvent) takes place. Then, the wash liquid collected at the bottom 4 of the absorption vessel is removed by suction and the gas is passed to the analyzer to be analyzed. After a constant value has been set on the NH$_3$ analyzer, the concentration is calculated according to the formula given above.

Figure 2:
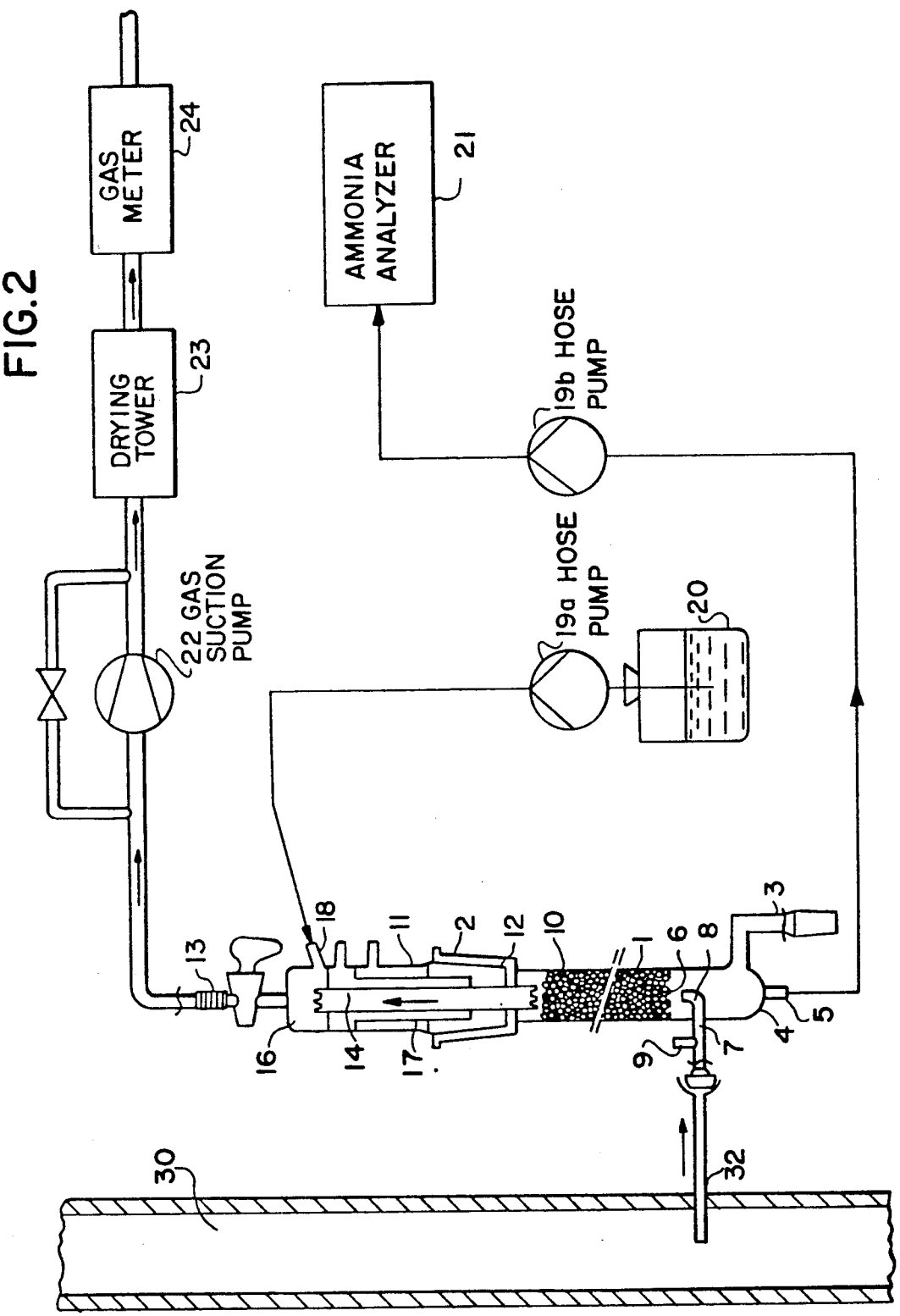
FIG. 2 shows one arrangement of the columnar absorption vessel in conjunction with a flue-gas conduit, a probe, and the other gas analyzing equipment.

The procedure for using the apparatus in accordance with the invention for the continuous determination of the ammonia concentration in gases in the ppm range is explained below with reference to FIG. 2.

The gas to be tested is drawn out of a flue gas conduit 30 and into the absorption column 1 by suction with the aid of gas pump 22 through a probe 32 and a gas line. The volume flow removed by suction can be regulated with a needle valve connected in a bypass to the gas pump 22. The volumetric flow rate of the gas to be tested may be varied over a wide range, for example in the case of the waste gas from a large industrial furnace system, between 5 and 200 l/h. A preferred volumetric flow rate is normally in the range of about 15-45 l/h. The gas removed by suction is introduced via connection pieces 7, 8 provided with a spherical groundglass joint into the absorption device. In the absorption device, the gas flows from below through a glass column 1 with a packing 10 and is brought into contact with a countercurrent flow of the absorption liquid supplied from above onto the packing 10 for the absorption of the ammonia.

Solutions of acids, such as H$_2$SO$_4$, H$_3$BO$_3$, or HCL, can be used, for example, as 1 molar aqueous solutions, as the absorption liquid. These solutions may also advantageously be used as the wash fluid in rinse line 9 as discussed above. The volume flow of the absorption liquid used in accordance with the above described system is in the range of about 0.03 and 1.0 l/h, and preferably from about 0.1 to 0.5 l/h. Again, these flow rates are for purposes of illustration and should not be construed as limiting this invention.

The absorption of the ammonia takes place in the following manner:

The absorption liquid is pumped by hose pump 19a out of a storage vessel 20 and onto the packing 10 via connection piece 18.

The liquid absorption agent drips through the packing 10, where it is charged with the NH$_3$ and falls onto the hemispherical bottom 4 of absorption column 1, and is collected. From there, a portion of the solution flows out of the column 1 through overflow 3. The other portion of the solution is removed via suction by means of a hose pump 19b and is pumped into an ammonia analyzer 21. The ammonia analyzer used in accordance with the preferred embodiment of the invention detects the ammonia concentration based on the principle of the gaseous diffusion of ammonia through a membrane with a subsequent conductometric determination of the ammonia content. The ammonia analyzer is an electric conductivity measuring device which includes a membrane located between two compartments. On one side of the membrane, an absorption fluid, such as ammonium hydroxide in boric acid, is present. Various amounts of ammonium hydroxide and boric acid concentrations are used, depending on the ammonia concentration to be measured. For example, from a 0-1 ppm measurement range, 3 ml of 0.02M NH$_4$OH per liter of 0.1% boric acid may advantageously be used. Likewise, for the range of 1-200 ppm ammonia, 5 ml of 0.02M NH$_4$OH per liter of 1% boric acid may advantageously be used. For the range of 1-1000 ppm ammonia, 15 ml of 0.02M NH$_4$OH per liter of 3% boric acid may advantageously be used.

On the other side of the membrane, a wash fluid including NH$_4$Cl is present. At this side, in the neighborhood of the membrane, KOH is added, thus developing NH$_3$ from the NH$_4$Cl. NH$_3$ diffuses through the membrane into the absorber fluid contained in the first-mentioned compartment. Thereby the conductivity of the absorption fluid is changed and an electric potential difference (a peak) between that fluid and the original absorption fluid is generated. This process is also used for calibration, whereby the NH$_4$Cl-concentration in the second compartment is raised in distinct subsequent steps. An ammonia analyzer of the type described above is commercially available, such as the Wescan 360 from the firm Gamma Analysentechnik. This ammonia analyzer is used in the preferred embodiment of the invention. Other types of ammonia analyzers may be used without departing from the invention.

The gas with the ammonia removed passes above the packing 10 through the cooler 11, and passes out of the apparatus via stopcock 13 and through the pump 22. The gas is then passed through a drying tower 23 filled with a drying agent and finally passed into a gas meter 24. Such drying towers, drying agents and gas meters are conventional and well known to those skilled in the art.

The invention will now be explained in further detail using a practical example of the method and apparatus in accordance with this invention.

EXAMPLE

The $NH_3$-determining apparatus was used for measuring the $NH_3$ loss in a system for testing catalysts for selective catalytic reduction processes (SCR catalysts) with flue gas. The theoretical $NH_3$ concentration was additionally determined wet-chemically ($=C_{NH_3}{}^G$, actual). The flue gas had the following composition.

$O_2 = 4.5\%$ by volume (dry basis)
$H_2O = 10\%$ by volume dry
$CO_2 = 11\%$ by volume dry
$SO_2 = 70$ ppm dry
$NO_x = 200$ ppm dry
$N_2 =$ remainder

TABLE 1

| EXAMPLE | WASH LIQUID EXAMPLE | $V_{Abs}$ | $V_G$ | $C_{NH_3}{}^G$ | $C_{NH_3}{}^G$ Actual |
|---|---|---|---|---|---|
| 1 | 1 m $H_2SO_4$ | 0.236 | 36.0 | 198.3 | 200 |
| 2 | 1 m $H_2SO_4$ | 0.238 | 58.0 | 19.6 | 20 |
| 3 | 1 m $H_2SO_4$ | 0.236 | 36.9 | 20.2 | 20 |
| 4 | 1 m $H_2SO_4$ | 0.236 | 37.0 | 10.3 | 10 |
| 5 | 1 m $H_2SO_4$ | 0.236 | 37.0 | 4.7 | 5 |
| 6 | 1 m $H_2SO_4$ | 0.236 | 37.0 | 1.9 | 2 |
| 7 | 1 m $H_3BO_3$ | 0.240 | 40.0 | 19.8 | 20 |
| 8 | 1 m $H_3BO_3$ | 0.237 | 40.0 | 4.9 | 5 |

As can be seen from the above data, the apparatus and process according to the invention provides an accurate determination of the ammonia content in the test gas ($C_{NH_3}{}^G$), when compared to the concentration determined by the standard wet chemical method ($C_{NH_3}{}^G$, actual). The data in Table 1 also demonstrated that the method and apparatus in accordance with the invention are accurate over a wide range of ammonia concentrations and at a low ammonia concentrations.

The entire priority document, German Patent Application No. P 40 10 425.7, is relied on and incorporated herein by reference.

Various modifications and changes may be made to the above described invention, without departing from the spirit and scope of the invention as described in the claims.

We claim:

1. A device for the continuous measurement of the ammonia concentration in gases, comprising: a columnar absorption vessel with an outlet piece located at a bottom of said absorption vessel; an overflow pipe located laterally above the bottom of said absorption vessel; an infeed pipe for admitting a gas to be measured into the absorption vessel above the bottom; a sieve bottom fastened in the vessel above the infeed pipe; said infeed pipe including a rinse line; said column definding an area for receiving a packing material, the area located above the sieve bottom and essentially occupies the entire absorption vessel; a cooling part which extends from the absorption vessel, said cooling part including a cooling zone, and a gas collection chamber located over said cooling zone; a connection piece for the supplying a liquid absorption agent into said gas collection chamber; an inner pipe which runs through said cooling zone and extends into the gas collection chamber, said inner pipe being tightly connected to a jacket of the cooling part.

2. The device according to claim 1, wherein the absorption vessel and the cooling part are designed as separate, individual pieces which are connectable to each other.

3. The device according to claim 2, wherein the absorption vessel and the cooling part are connectable via ground-glass joints.

4. The device according to claim 1, wherein the bottom of the absorption vessel is in the shape of a hemisphere, wherein the outlet piece extends from the bottom of the hemisphere.

5. The device according to claim 1, wherein the infeed pipe is located between the bottom of the absortion vessel and the sieve bottom.

6. The device according to claim 5, wherein the infeed pipe is L-shaped.

7. The device according to claim 6, wherein the infeed pipe introduces the gas to be analyzed in a central portion of the absorption column, with respect to the cross section of the absorption column.

8. The device according to claim 1, wherein a closable suction piece extends from the gas collection chamber.

9. The device according to claim 8, wherein said suction piece is closable by means of a stopcock.

10. The device according to claim 1, wherein said inner pipe includes a serrated crown on at least one of its ends.

11. The device according to claim 1, wherein said inner pipe has a serrated crown on each of its ends.

12. The device according to claim 1, wherein said inner pipe is tightly connected to said cooling part below said cooling zone.

13. The device according to claim 1, wherein said area is filled with a packing material.

14. A device for the continuous measurement of the ammonia concentration in gases, comprising: a columnar absorption vessel having a hemispherical shaped bottom; an outlet piece located at the bottom; an overflow pipe located laterally above the bottom; an infeed pipe for admitting a gas to be measured into the absorption vessel above the bottom and below a sieve bottom fastened in the absorption vessel; said infeed pipe being L-shaped and centrally located in the vessel and said infeed pipe further including a rinse line; said column definding an area for receiving a packing material, the area located above the sieve bottom and essentially occupies the entire absorption vessel; a cooling part which extends from the absorption vessel, said cooling part including a cooling zone, and a gas collection chamber located over said cooling zone; a closable suction piece extending from said gas collection chamber; a connection piece for supplying a liquid absorption agent into said gas collection chamber; an inner pipe which includes a serrated crown on at least one of its ends, said inner pipe extending through the cooling zone, with one end extending into the gas collection chamber and the other end being tightly connected to a jacket of the cooling part below the cooling zone.

15. A method for the continuous measurement of the ammonia concentration in gases, comprising: contacting a volume flow of a gas to be measurement with a countercurrent flow of a liquid absorption agent; quantitatively measuring the ammonia concentration of at least a part of the absorption agent in an ammonia analyzer, after it has contacted the gas to be measured; measuring the volume flow rate of the absorption agent; measuring the volume flow rate of the gas freed of ammonia; and calculating the NH$_3$ concentration according to the formula:

$$C^G_{NH3} = \frac{C^L_{NH3} \times V_{Abs} \times 10^6 \times V_{M,NH3}}{V_G \times M_{NH3}} \text{ (ppm)}$$

in which:

$C_{NH3}^G$ = concentration of NH$_3$ in the gas (ppm relative to dry);

$C_{NH3}^L$ = concentration of NH$_3$ in the absorption solution (g/dm$^3$);

$V_{Abs}$ = volume flow of the flowing absorption solution (dm$^3$/h);

$V_G$ = volume flow of the gas to be analyzed, drawn by suction through the absorption vessel (dm$^3$/h in a normal state relative to dry);

$V_{M,NH3}$ = molar volume of gaseous ammonia state (dm$^3$/mole in a normal state); and $M_{NH3}$ = molar mass of ammonia (g/mole).

16. The method according to claim 15, wherein the gas freed of ammonia is dried prior to measuring its volume flow rate.

17. The method according to claim 15, wherein the gas to be measured is taken from a flue-gas conduit.

18. The method according to claim 15, wherein the ammonia concentration is quantitatively measured by diffusing the gas through a membrane and subsequently using a conductometric determination of the ammonia content.

19. The method according to claim 15, wherein the ammonia concentration is meaured in the parts per million range.

20. The method according to claim 15, wherein the ammonia containing gas is admitted at a bottom portion of an absorption column and the liquid absorption agent is admitted at a top portion of the absorption column prior to the contacting step.

21. The method according to claim 15, further comprising adjusting a base line of the ammonia analyzer by drawing in a fresh wash liquid and calibrating the ammonia analyzer with a standard solution prior to the contacting step.

* * * * *

UNITED STATES PATENT AND TRADEMARK OFFICE
CERTIFICATE OF CORRECTION

PATENT NO. : 5,131,260
DATED : July 21, 1992
INVENTOR(S) : Brand et al.

It is certified that error appears in the above-identified patent and that said Letters Patent is hereby corrected as shown below:

On the Title page, item [75] inventors:

Change "Wolfgang Honen" to --Wolfgang Honnen--.

Signed and Sealed this

Twenty-first Day of September, 1993

Attest:

BRUCE LEHMAN

*Attesting Officer*  *Commissioner of Patents and Trademarks*